US00PP12570P2

(12) United States Plant Patent
Bradford

(10) Patent No.: US PP12,570 P2
(45) Date of Patent: Apr. 23, 2002

(54) PEACH TREE NAMED 'SNOW PRINCESS'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 09/722,237

(22) Filed: Nov. 27, 2000

(51) Int. Cl.[7] ..... A01H 5/00
(52) U.S. Cl. ..... Plt./196
(58) Field of Search ..... Plt./196

(56) References Cited

U.S. PATENT DOCUMENTS

PP7,066 P 12/1989 Bradford et al.
PP9,515 P 4/1996 Bradford et al.

*Primary Examiner*—Bruce R. Campell
*Assistant Examiner*—Susan B. McCormick

(57) ABSTRACT

The present invention relates to a peach tree, *Prunus persica*, and more particularly to a new and distinct variety broadly characterized by a medium size, vigorous, hardy, self-fertile, productive and regular bearing tree. The fruit matures under the ecological conditions described approximately the third week in July, with first picking on Jul. 20, 2000. The fruit is uniformly large in size, very good in flavor, globose in shape, freestone in type, firm in texture, white in flesh color, and mostly red in skin color. The variety was developed as a first generation cross using Diamond Princess (U.S. Plant Pat. No. 7,066) yellow flesh peach as the selected seed parent and an unnamed white flesh peach as the selected pollen parent.

1 Drawing Sheet

BACKGROUND OF THE VARIETY

In a continuing effort to improve the quality of shipping fruits, I, the inventor, typically hybridize a large number of nectarine, peach, plum, apricot, and cherry seedlings each year. The present invention relates to a new and distinct variety of peach tree, which has been denominated varietally as 'SNOW PRINCESS'. The present variety was hybridized by me in 1992, grown as a seedling on its own root in my greenhouse, and transplanted to a cultivated area of our experimental orchard at Bradford Farms near Le Grand, Calif. in Merced County (San Joaquin Valley). It was developed as a first generation cross using Diamond Princess (U.S. Plant Pat. No. 7,066) yellow flesh peach as the selected seed parent and an unnamed white flesh peach as the selected pollen parent. Subsequent to origination of the present variety of peach tree, I asexually reproduced it by budding and grafting in the experimental orchard described above, and such reproduction of plant and fruit characteristics were true to the original plant in all respects. The reproduction of the variety included the use of Nemaguard Rootstock (unpatented) upon which the present variety was compatible and true to type.

The present variety is similar to its selected seed parent, Diamond Princess (U.S. Plant Pat. No. 7,066) peach, by producing freestone peaches that are globose in shape, firm in texture, and mostly red in skin color, but is distinguished therefrom and an improvement thereon by producing fruit that is white instead of yellow in flesh color, that is subacid instead of acid in flavor, that is larger in size, and that matures about two weeks later.

The present variety is most similar to White Princess (U.S. Plant Pat. No. 9,515) peach by producing freestone peaches that are white in flesh color, subacid and sweet in flavor, and mostly red in skin color, but is distinguished therefrom and an improvement thereon by blooming about ten days earlier, by having reniform instead of globose glands, and by producing fruit that is much larger in size and that matures about three weeks earlier.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Jul. 24, 2000 on the original tree during its seventh growing season. All major color code designations are by reference to the Inter-Society Color Council, National Bureau of Standards. Common color names are also used occasionally.

TREE

Size: Medium, reaching and maintaining a height of 10' [3.05 m.] after seven growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase formed.

Hardiness: Hardy with respect to central California winters.

Heat tolerance: Observed to perform adequately in typical central California climatic conditions, which typically include prolonged periods of heat.

Drought tolerance: Variety is developed for commercial orchards and requires regular irrigation.

Production: Very productive, thinning necessary.
Fertility: Self-fertile.
Bearing: Regular bearer with no alternate bearing yet observed.
Trunk:
*Size.*—Medium, reaching a maximum diameter of 5" [127 mm.] after the seventh growing season.
*Texture.*—Rough.
*Bark color.*—Dark grayish yellowish brown [81. d.gy.yBr].
*Lenticels.*—Numerous. Color: Strong yellowish brown [74. s.yBr]. Typical Size: ¼" to 7/16" [6.4–11.1 mm.].
Branches:
*Size.*—Diameter of scaffold is 3" [76 mm.] measured 12" above the crotch, typical of *Prunus persica*, and dependent upon cultural practices and climatic conditions.
*Texture.*—Smooth on 1st year wood, increasing roughness with age.
*Color.*—1st Year Wood Topside: Grayish red [19. gy.R]. 1st Year Wood Underside: Brilliant yellow green [116. brill.YG]. Older wood: Dark yellowish brown [78. d.yBr].
*Lenticels.*—Numerous. Color: Moderate orange yellow [71. m.OY]. Typical Size: 1/16" to ¼" [1.6–6.4 mm].
Leaves:
*Size.*—Large. Average Length: 6" [152 mm.]. Average Width: 1½" [38.1 mm.].
*Arrangement.*—Alternate.
*Thickness.*—Medium.
*Form.*—Elliptical.
*Apex.*—Acuminate.
*Base.*—Acute.
*Surface.*—Smooth.
*Color.*—Dorsal Surface: Very dark yellowish green [138. v.d.yG]. Ventral Surface: Moderate yellowish green [136. m.yG].
*Margin.*—Finely serrate.
*Venation.*—Pinnately net veined.
*Petiole.*—Average length: 7/16" [11.1 mm.]. Average thickness: 1/16" [1.6 mm.]. Color: Light yellow green [119. l.YG].
*Stipules.*—Numerous, 2 per leaf, up to 6 per growing tip. Average Length: ¼" [6.4 mm.]. Color: Light yellow green [119. l.YG].
*Glands.*—Numbers: 2 to 6, but most often 2. Position: Usually alternate, occasionally opposite, positioned both on the petiole and the base of blade. Size: Medium. Form: Reniform. Color: Brilliant yellow green [116. brill.YG].
*Leaf buds.*—Pointed.
Flower buds:
*Hardiness.*—Hardy, with respect to central California winters.
*Diameter.*—Typically ⅜" [9.5 mm.] 1 week before bloom.
*Length.*—Typically ¾" [19.1 mm.] 1 week before bloom.
*Form.*—Free.
*Surface.*—Pubescent.
*Color.*—Moderate purplish red [258. m.pR].
Flowers: Perfect, complete, perigynous, usually a single pistil, typically thirty or more stamens, five sepals and petal locations alternately positioned.
*Type.*—Showy.
*Average flower diameter.*—1¾" [44.5 mm.].
*Number of petals.*—Usually five, very few doubles.
*Petal shape.*—Circular.
*Petal margin.*—Slightly wavy.
*Average petal diameter.*—11/16" [17.5 mm.].
*Average petal length.*—11/16" [17.5 mm.]; Petal Apex. — Rounded.; Petal Base. — Acute.
*Petal color.*—Pale purplish pink [252. p.pPk].
*Anther color.*—Dark red [16. d.R] when first open.
*Stigma color.*—Moderate yellow [87. m.Y].
*Sepal color.*—Grayish purplish red [262. gy.pR].
*Sepal length.*—7/32" [6 mm.].; Sepal Width. — 5/32" [4 mm.].
*Average pistil length.*—¾" [19.1 mm.].
*Average stamen length.*—⅝" [15.9 mm.].
*Fragrance.*—Moderate when nectar is present.
*Blooming period.*—Early compared with other varieties.
*Onset of bloom.*—One percent on Feb. 17, 2000.
*Duration of bloom.*—One to two weeks, dependent on ambient temperature.

FRUIT

Maturity when described: Firm ripe, Jul. 24, 2000.
Date of first picking: Jul. 20, 2000.
Date of last picking: Jul. 29, 2000.
Size: Uniform. large.
*Average diameter axially.*—3¼" [82.6 mm.].
*Average diameter across suture plane.*—3½" [88.9 mm.].
*Typical weight.*—11.9 ounces [337 grams].
Form: Uniform, symmetrical, globose with slight axial compression.
*Longitudinal section form.*—Round.
*Transverse section through diameter.*—Round.
Suture: An inconspicuous line extending from the base to the pistil point with some shallow grooving near the base and toward the apex.
Ventral surface: Strongly rounded, very slightly lipped toward the apex.
Lips: Slightly unequal.
Cavity: Flaring, elongated in the suture plane, suture showing on one side, Pale yellowish pink [31. p.yPk] stem markings typical.
*Depth.*—½" [12.7 mm.].
*Breadth.*—1⅛" [28.6 mm.].
Base: Rounded to slightly truncate.
Apex: Rounded.
Pistil point: Apical, negligible in length.
Stem: Medium.
*Average length.*—⅜" [9.5 mm.].
*Average width.*—3/16" [4.8 mm.].
Skin:
*Thickness.*—Medium.
*Texture.*—Pubescent.
*Tenacity.*—Tenacious to flesh.
*Astringency.*—Slight to none.
*Tendency to crack.*—None observed.
*Color.*—Moderate red [15. m.R] where exposed to sunlight smoothly blending into Moderate pink [5. m.Pk] where sun protected with some Light orange yellow [70. l.OY] freckling toward the apex.
Down: Scant, short, does not roll up when rubbed.
Flesh:
*Color.*—Yellowish white [92. yWhite] with some Dark red [16. d.R] streaking close to the stone.

*Surface of pit cavity.*—Dark red [16. d.R] fibers cleanly detaching from the stone.
*Amygdalin.*—Scarce.
*Juice.*—Moderate, rich.
*Texture.*—Firm, crisp.
*Fibers.*—Abundant, fine.
*Ripens.*—Slightly earliest toward the apex.
*Flavor.*—Subacidic and sweet, ranging from 14 to 19 brix.
*Aroma.*—Slight.
*Eating quality.*—Very good.

STONE

Type: Freestone.
Form: Elliptical.
Base: Straight.
Apex: Acute to acuminate.
Sides: Slightly unequal.
Surface: Irregularly furrowed near the apex and pitted toward the base.
Ridges: Jagged toward the base.
Color: Dark brown [59. d.Br].
Average pit wall thickness: ¼" [6.4 mm.].
Average width: 1" [25.4 mm.].
Average length: 1 7/16" [36.5 mm.].
Tendency to split: None observed.
Kernel:
*Form.*—Oval.
*Color.*—Pale yellow [89. p.y] with Deep orange yellow [69. deep OY] veins when first exposed.
*Taste.*—Very bitter.
*Viable.*—Yes.
*Average width.*—½" [12.7 mm.].
*Average length.*—¾" [19.1 mm.].
Pellicle color: Grayish brown [61. gy.Br].
Amygdalin: Abundant.

USE

Market: Fresh and long distance shipping.
Keeping quality: Fruit quality observed to remain in good condition in excess of 20 days in standard cold room at 36° Fahrenheit [2° Celsius].
Resistance to insects: No unusual susceptibilities noted.
Resistance to diseases: No unusual susceptibilities noted.

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is most similar to White Princess (U.S. Plant Pat. No. 9,515) peach by producing freestone peaches that are white in flesh color, subacid and sweet in flavor, and mostly red in skin color, but is distinguished therefrom and an improvement thereon by blooming about ten days earlier, by having reniform instead of globose glands, and by producing fruit that is much larger in size and that matures about three weeks earlier.

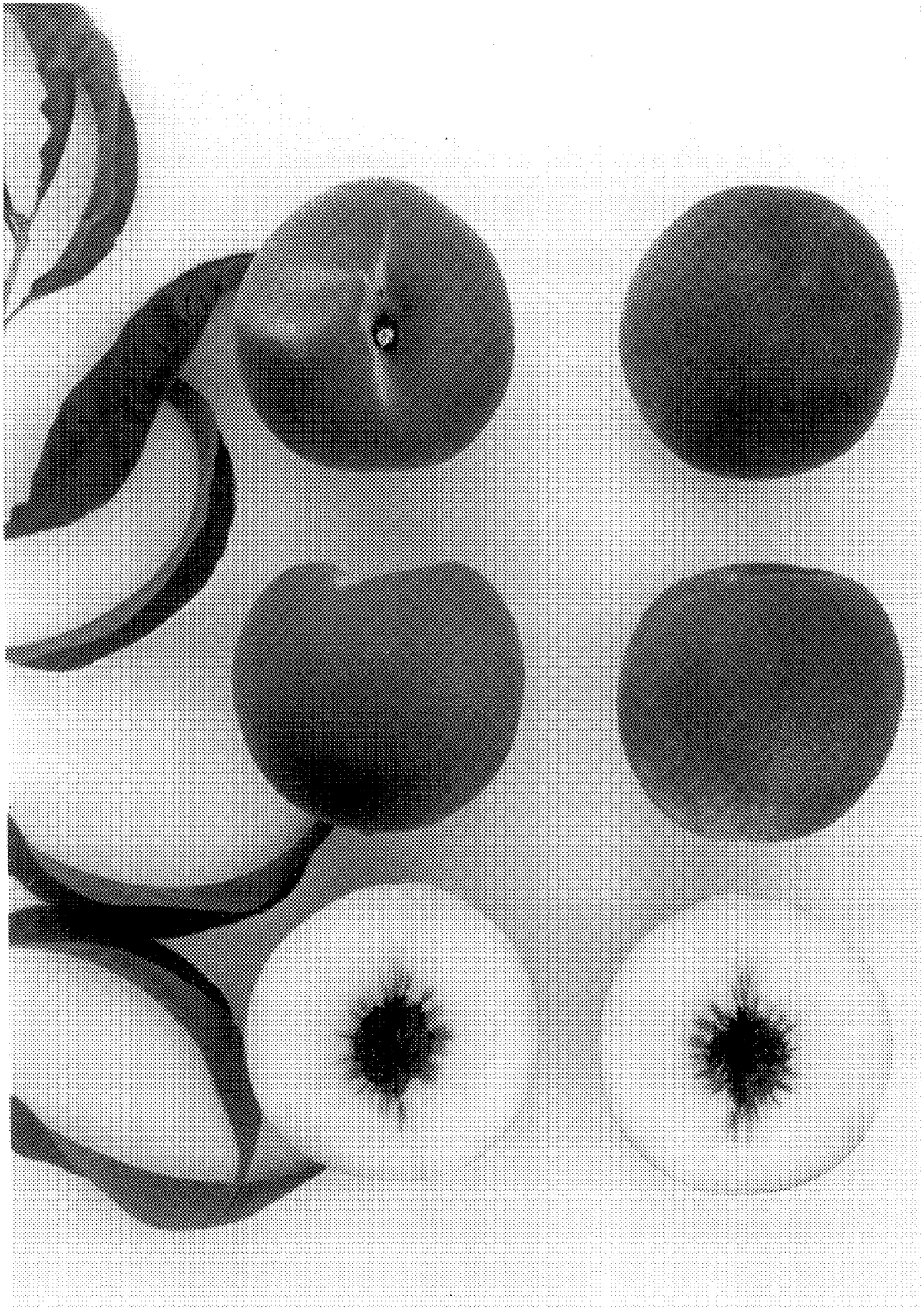

* * * * *